United States Patent [19]
Brodsky

[11] Patent Number: 4,927,415
[45] Date of Patent: May 22, 1990

[54] APPARATUS FOR SAFE USE AND DISPOSAL OF NEEDLES

[76] Inventor: Stuart A. Brodsky, 2556-H Navarra Dr., Carlsbad, Calif. 92009

[21] Appl. No.: 231,782

[22] Filed: Aug. 12, 1988

[51] Int. Cl.$^5$ .............................................. A61M 5/18
[52] U.S. Cl. .................................... 604/164; 604/171; 604/198; 128/919
[58] Field of Search ........................ 604/110, 164–165, 604/171–172, 198, 263

[56] References Cited

U.S. PATENT DOCUMENTS

| | | | |
|---|---|---|---|
| 3,421,509 | 1/1969 | Fiore | 604/171 |
| 3,592,192 | 7/1971 | Harautuneian | 604/165 |
| 4,160,450 | 7/1979 | Doherty | 604/164 |
| 4,266,543 | 5/1981 | Blum | 128/218 N |
| 4,631,057 | 12/1985 | Mitchell | 604/198 |
| 4,643,200 | 2/1987 | Jennings, Jr. | 128/763 |
| 4,655,751 | 4/1987 | Harbaugh | 604/198 |
| 4,664,654 | 5/1987 | Strauss | 604/198 |
| 4,676,783 | 6/1987 | Jagger et al. | 604/171 |
| 4,692,154 | 9/1987 | Singery et al. | 604/172 X |
| 4,778,453 | 10/1988 | Lopez | 604/110 |
| 4,781,692 | 11/1988 | Jagger et al. | 604/171 X |

*Primary Examiner*—C. Fred Rosenbaum
*Assistant Examiner*—C. Maglione
*Attorney, Agent, or Firm*—Deborah A. Peacock; Robert W. Weig

[57] ABSTRACT

The disclosure is directed to an apparatus for preventing needle pricks and for safely disposing used intravenous needles. The apparatus comprises a longitudinal body, having first and second ends, an entry and closure mechanism on the first end and an aperture on the second end of the longitudinal body, and a pulling structure which passes through the interior and both ends of the longitudinal body. The pulling structure is attachable to an intravenous needle. The other end of the pulling structure may be attached to a syringe or blood-drawing device. A user pulls on the pulling structure to draw the intravenous needle into the longitudinal body after use. The entry and closure mechanism prevents the needle from exiting the longitudinal body after it becomes disposed within the longitudinal body. The longitudinal body, containing the needle within, can then be disposed of.

21 Claims, 1 Drawing Sheet

APPARATUS FOR SAFE USE AND DISPOSAL OF NEEDLES

BACKGROUND OF THE INVENTION

1. Field of the Invention.

This invention relates to an apparatus for safely using and disposing of intravenous needles.

2. Description of the Prior Art. The need exists in the art to protect doctors, nurses, other health practitioners, and others who may come into contact with used needles, from being pricked with needles after the needles have been used intravenously. In particular, an apparatus is needed to prevent needle pricks during or directly after use of needles to thereby prevent the transmission of blood-carried diseases or organisms via used needles, such as hepatitis and HIV (the AIDS related virus). The need also exists in the art to safely dispose of needles after they have been used, so that others, such as waste handlers, do not accidentally get pricked with the needles and thereby exposed to blood-carried diseases or organisms.

A common practice in the art is to cut needles so that they can't be reused. However, this practice may even increase the chances of a health practitioner getting pricked with a needle and certainly does not prevent accidental pricks after disposal.

Several devices have been developed in the art which provide a sheath member around the used needle, to prevent needle pricks. The most common device in the art is a needle cap which is removed from the needle before use and placed back on the needle after use for disposal. However, practitioners often stick themselves with needles when they replace this cap. Moreover, the cap can be removed after disposal, thereby potentially exposing others to needle pricks. Mounted devices exist in the art for preventing needle pricks when the cap is replaced; these mounted devices consist of circular holders for holding the cap while the needle is replaced in the cap, so that the practitioner does not need to hold the cap. However, if the cap is not seated correctly within the holder, the practitioner may have to use his or her hand to hold the cap, thereby defeating the purpose of the mounted device. Moreover, these devices are permanently mounted and thus not useful in situations requiring more mobility for the practitioner, such as in a hospital room.

Another practice to prevent needle pricks is to have the practitioner discard uncapped or unsheathed needles into a waste bin. However, this often does not protect waste handlers from being pricked with needles Several syringes or blood-drawing devices have been developed in the art to provide a sheath or guard which can be extended or forced over the needle after use. Such devices are represented in U.S. Pat. No. 4,631,057, entitled "Shielded Needle," to Mitchell; U.S. Pat. No. 4,643,200, entitled "Safety Blood Donor Apparatus," to Jennings, Jr.; U.S. Pat. No. 4,655,751, entitled "Liquid Dispensing and Receiving Syringe," to Harbaugh; U.S. Pat. No. 4,664,654, entitled "Automatic Protracting and Locking Hypodermic Needle Guard," to Strauss; and U.S. Pat. No. 4,676,783, entitled "Retractable Safety Needle," to Jagger, et al. The guards on these devices are not retrofittable with conventional syringes or blood-drawing devices; thus the devices cannot be utilized in all situations with conventional needles. Also, in the '057, '751, '654, and 783 Patents, the open ends of the guards do not prevent fluids from dripping out. Another device is disclosed in U.S. Pat. No. 4,266,543, entitled "Hypodermic Needle Protection Means," to Blum, which teaches pushing the needle against a hard surface for allowing the needle to be forced into a housing. This device, however, may cause a practitioner to get pricked with the needle if the hard surface is not adequate. Also, there is no assurance that the needle will go completely into the housing and a careless practitioner may dispose the needle/housing arrangement with the needle sticking partially out. Furthermore, as with the devices discussed above, this housing cannot be utilized with standard intravenous needles; the needle/housing arrangement must be purchased and used as a single unit.

Thus, the need exists in the art to provide an apparatus, which can be used with conventional needles, for safely disposing used needles and for preventing needle pricks. An apparatus which also prevents fluids from dripping off the needles and out of associated tubing is also needed.

SUMMARY OF THE INVENTION

This invention relates to an apparatus for the safe use and disposal of an intravenous needle. The apparatus comprises needle-safe containment means comprising a longitudinal body having first and second ends, entry and closure means disposed at the first end for allowing the needle to enter the longitudinal body and for denying exit of the needle therethrough, and aperture means at the second end of the longitudinal body; and discrete needle pulling means attachable to the needle and passed through the entry and closure means and the aperture means for drawing the needle into the longitudinal body for safe positioning and disposal of the needle within the needle-safe containment means after use of the needle. The longitudinal body is preferably generally tubular in shape and comprises a puncture-resistant material, such as plastic, rubber, vinyl, or the like.

The entry and closure means preferably comprises a plurality of overlapping flaps to allow the needle to pass therethrough from outside the longitudinal body into the longitudinal body and deny exit of the needle therethrough. These overlapping flaps fold or collapse inward as the needle passe into the longitudinal body, and then come back together to prevent the needle from exiting the longitudinal body.

The apparatus preferably comprises stopping means to prevent the needle from being pulled from the longitudinal body through the second end thereof. The needle pulling means may comprise these stopping means which engage the longitudinal body during the pulling of the needle through the longitudinal body. Alternatively, stopping means may be disposed at the second end and within the longitudinal body.

The needle pulling means may be removably attachable to the needle. In an alternative embodiment, the apparatus further comprises the needle, and the needle is attached to the needle pulling means. The needle pulling means is preferably hollow tubing, useful for carrying fluids to or from a patient. The needle pulling means or hollow tubing exiting the second end may be attachable to fluid movement devices, such as a syringe or blood-drawing device.

The needle may be a hypodermic needle or a trocar/cannula arrangement. For a trocar/cannula arrangement, when the needle pulling means is pulled, the trocar is drawn into the longitudinal body and the cannula is left in place within a patient.

Accordingly, it is a primary object of the present invention to provide an apparatus for preventing needle pricks from intravenous needles and for safely disposing the intravenous needles after use.

It is another object of the present invention to provide an apparatus for preventing needle pricks which is easy to manufacture and use.

Yet another object of the present invention is to provide an apparatus which can be used with conventional intravenous needles.

An advantage of the apparatus of the present invention is that it is easy to use and protects health practitioners, waste handlers, and others from being pricked with needles.

Another advantage of the present invention is that it retains fluids from dripping needles an tubing.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention.

DESCRIPTION OF THE PREFERRED EMBODIMENT OF THE INVENTION

This invention relates to an apparatus for the safe use and disposal of intravenous needles. The apparatus of the invention comprises needle-safe containment means comprising a longitudinal body having first and second ends, entry and closure means disposed at the first end for allowing the needle to enter the longitudinal body and for denying exit of the needle therethrough, and aperture means at the second end of the longitudinal body; and needle pulling means attachable to the discrete needle and passed through the entry and closure means and the aperture means for drawing the needle into the longitudinal body for safe positioning and disposal of the needle within the needle-safe containment means after use of the needle.

Figure 1:
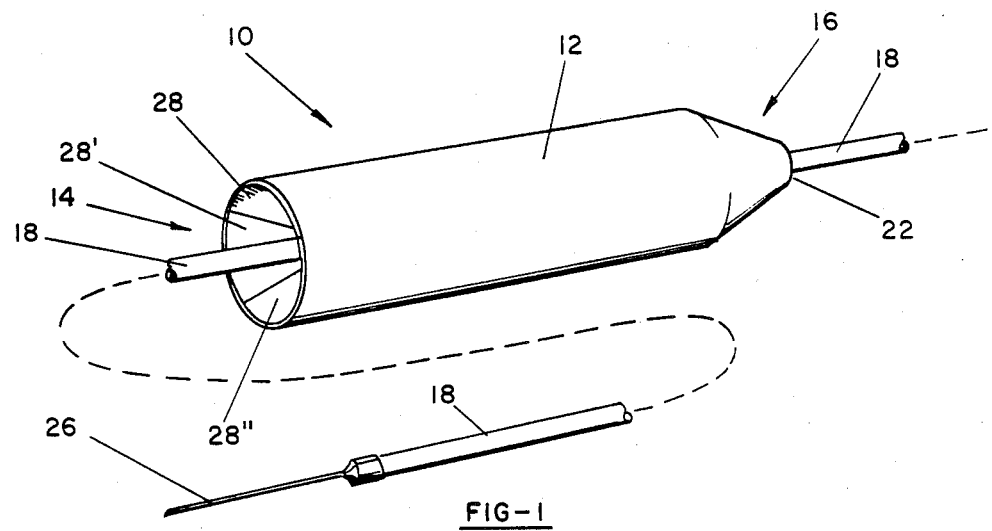
FIG. 1 is an isometric view of the preferred embodiment of the invention, showing a needle outside the longitudinal body.
Figure 2:
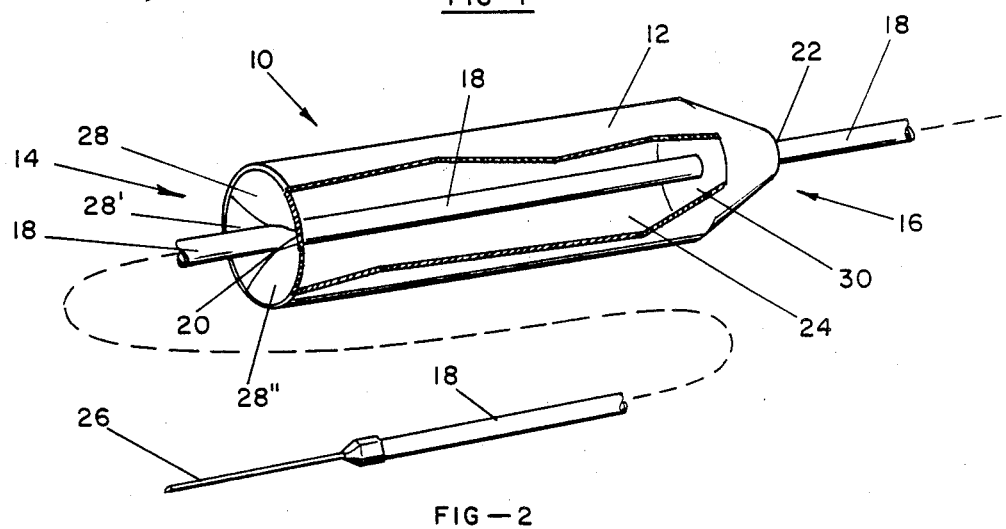
FIG. 2 is a cutaway view of the embodiment of FIG. 1.
Figure 3:
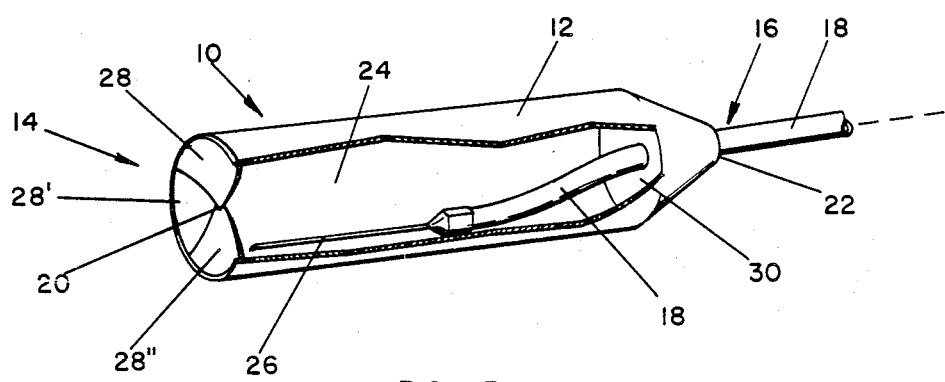
FIG. 3 is a cutaway view of the embodiment of FIG. 1, showing the needle after being drawn into the longitudinal body.

Reference is now made to FIGS. 1-3 which illustrate the preferred embodiment of the apparatus 10 of the invention. The longitudinal body 12 is generally tubular in shape and preferably comprises a puncture-resistant material, such as plastic, rubber, vinyl, or the like. The longitudinal body 12 has a first end 14 and a second end 16. Pulling means, such as hollow tubing 18 passes through an entry and closure opening 20 at the first end 14 and an aperture 22 at the second end 16 and through the interior 24 of the longitudinal body 12. The hollow tubing 18 at the first end 14 is attachable to a needle 26.

FIGS. 1 and 2 show a needle 26 prior to or just after use. After the needle 26 is used, a user holds the longitudinal body 12 with one hand and pulls on the hollow tubing 18 with another hand which allows the needle 26 to slide through the entry and closure opening 20 and into the interior 24 of the longitudinal body 12. FIG. 3 shows the needle 26 disposed within the interior 24 of the longitudinal body 12 for disposal. As can be seen, the user does not come into contact with the needle 26 and thus will not be pricked with the needle 26. Likewise, the longitudinal body 12 prevents others, such as waste handlers, from being pricked with the needle 26 after disposal.

The entry and closure opening 20 allows entry of the needle 26 into the interior 24 of the longitudinal body 12, and also prevents the needle 26 from exiting the longitudinal body 12 once it becomes disposed therein. The preferred entry and closure opening, shown in the drawings, comprises a plurality of overlapping flaps (for example, see 28, 28', and 28") which fold inward as the hollow tubing 18 and needle 26 are pulled through the entry and closure opening 20 into the interior 24 of the longitudinal body 12 (see FIGS. 1 and 2) and close back together after the needle 26 has completely passed through the entry and closure opening 20 and is disposed within the interior 24 of the longitudinal body 12 (see FIG. 3). Such flaps 28, 28' and 28" would need to be made of a resilient material, such as plastic, vinyl, rubber, or the like, so that they can fold inward and then come back together. As can be appreciated by those skilled in the art any number of flaps may be utilized and the invention is not limited to the number of flaps depicted in the drawing. Likewise, other entry and closure means can be utilized in accordance with the invention, as long as such entry and closure means allows entry of the needle into the longitudinal body and prevents exit therefrom.

In the preferred embodiment, the invention further comprises stopping means 30 for preventing the needle 26 from passing through the aperture 22 at the second end 16 after the pulling means 18 has drawn the needle 26 into the longitudinal body 12. The stopping means 30 may be slidably attached to the pulling means 18 on the interior 24 of the longitudinal body 12 so that when the needle 26 is pulled into the interior 24 of the longitudinal body 12, the stopping means 30 engages with the longitudinal body 12, thereby stopping any further pulling and preventing the needle 26 from exiting the aperture 22 at the second end 16. In an alternative embodiment, the stopping means 30 may be disposed within the interior 24 of the longitudinal body 12 at the second end 16 to stop the needle 26 from exiting the second end 16.

In one embodiment of the invention, the pulling means 18 is removably attachable to a needle 26. In such an embodiment, the apparatus is usable with conventional needles, available in the art. In an alternative embodiment, the apparatus of the invention includes a needle so that the attachment to a needle is not necessary.

The apparatus of the invention can be used with an type of needle common to the art, such as an intravenous needle, hypodermic needle, a trocar/cannula arrangement, etc. The drawings show only one type of needle, but the invention is not limited to any particular type or types of needles. In a trocar/cannula arrangement, commonly used for introducing intravenous fluids to a patient, the trocar (usually a rigid metal needle), surrounded by the cannula (a pliable hollow sheath), is inserted into the patient's vein. The trocar is then removed, leaving the cannula behind in the patient's vein. Because the cannula is pliable, the patient is more comfortable when the body, containing the cannula, is moved. The apparatus of the invention is useful for disposing the trocar portion once it is removed from the patient.

The term "intravenous," used throughout the specification and claims, is intended primarily to mean intravenous use of a needle for a patient, human or animal, however, this term is also intended to include uses of a needle which are potentially dangerous or harmful if a person can be pricked with the needle. For instance, needles may be used in chemical or biochemical applications, in which the user may be harmed by, for example, toxic substances if pricked with the needle.

When fluid needs to be introduced to or taken from a patient or other source, the preferred pulling means, as shown in the drawings, is hollow tubing 18 through which the fluid passes. With the hollow tubing 18 at the first end 14 attached or attachable to a needle 26, the hollow tubing 18 at the second end 16 can be attached to fluid movement means, such as a syringe or blood-drawing device (not shown). The apparatus of the invention may comprise fluid movement means, or may be removably attachable to fluid movement means. As can be appreciated by those skilled in the art, if fluid movement is not desired, the pulling means need not be hollow tubing, but can be any type of pulling device, such as a wire or line (not shown).

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. An apparatus for the safe use and disposal of a needle comprising:
    needle-safe containment means comprising a longitudinal body having first and second ends, entry and closure means disposed at said first end for allowing the needle to enter said longitudinal body and for denying exit of the needle therethrough, and aperture means at said second end of said longitudinal body; and
    discrete needle pulling means attachable to the needle and passed through said entry and closure means and said aperture means for drawing the needle into said longitudinal body for safe positioning and disposal of the needle within said needle-safe containment means after use of the needle.

2. An apparatus in accordance with claim 1 wherein said longitudinal body is generally tubular in shape.

3. An apparatus in accordance with claim 1 wherein said longitudinal body comprises a puncture-resistant material.

4. An apparatus in accordance with claim 3 wherein said puncture-resistant material comprises at least one member selected from the group consisting of plastic, rubber, and vinyl.

5. An apparatus in accordance with claim 1 wherein said entry and closure means comprises a plurality of overlapping flaps to allow the needle to pass therethrough from outside said longitudinal body into said longitudinal body and deny exit of the needle therethrough.

6. An apparatus in accordance with claim 1 wherein said needle pulling means comprises stopping means which engage the longitudinal body during the pulling of the needle through the longitudinal body to stop the needle from being pulled from said longitudinal body through said second end thereof.

7. An apparatus in accordance with claim 1 further comprising stopping means disposed at said second end and within said longitudinal body, to stop the needle from being pulled from said longitudinal body through said second end thereof.

8. An apparatus in accordance with claim 1 wherein said needle pulling means is removably attachable to said needle.

9. An apparatus in accordance with claim 1 wherein said needle pulling means is hollow tubing, useful for carrying fluids to or from a patient.

10. An apparatus in accordance with claim 9 wherein said hollow tubing exiting said second end is attachable to a syringe.

11. An apparatus in accordance with claim 1 wherein said needle is a trocar/cannula arrangement and when the needle pulling means is pulled the trocar is drawn into the longitudinal body and the cannula in left in place within a patient.

12. An apparatus for the safe use of an intravenous needle and the safe disposal of said intravenous needle comprising:
    a needle;
    needle-safe containment means comprising a longitudinal body having first and second ends, entry and closure means disposed at said first end for allowing said needle to enter said longitudinal body and for denying exit of said needle therethrough, and aperture means at said second end of said longitudinal body; and
    discrete needle pulling means attached to said needle and passed through said entry and closure means and said aperture means for drawing said needle into said longitudinal body for safe positioning and disposal of said needle within said needle-safe containment means after use of said needle.

13. An apparatus in accordance with claim 12 wherein said longitudinal body is generally tubular in shape.

14. An apparatus in accordance with claim 12 wherein said entry and closure means comprises a plurality of overlapping flaps to allow the needle to pass therethrough from outside said longitudinal body into said longitudinal body and deny exit of the needle therethrough.

15. An apparatus in accordance with claim 12 wherein said needle pulling means comprises stopping means which engage the longitudinal body during the pulling of the needle through the longitudinal body to stop the needle from being pulled from said longitudinal body through said second end thereof.

16. An apparatus in accordance with claim 12 further comprising stopping means disposed at said second end and within said longitudinal body, to stop the needle from being pulled from said longitudinal body through said second end thereof.

17. An apparatus for the use of safely administering or withdrawing fluids through an intravenous needle and the safe disposal of said intravenous needle comprising:
    an intravenous needle;

needle-safe containment means comprising a longitudinal body having first and second ends, entry and closure means disposed at said first end for allowing said needle to enter said longitudinal body and for denying exit of said needle therethrough, and aperture means at said second end of said longitudinal body;

discrete needle pulling means attached to said needle and passed through said entry and closure means and said aperture means for drawing said needle into said longitudinal body for safe positioning and disposal of said needle within said needle-safe containment means after use of said needle;

fluid movement means attached to said needle pulling means exiting said second end of said longitudinal body for causing fluid to flow into or from a patient.

18. An apparatus in accordance with claim 17 wherein said longitudinal body is generally tubular in shape.

19. An apparatus in accordance with claim 17 wherein said entry and closure means comprises a plurality of overlapping flaps to allow the needle to pass therethrough from outside said longitudinal body into said longitudinal body and deny exit of the needle therethrough.

20. An apparatus in accordance with claim 17 wherein said fluid movement means comprises a syringe.

21. An apparatus in accordance with claim 17 wherein said fluid movement means comprises a blood-drawing device.

* * * * *